United States Patent [19]

Grous et al.

[11] Patent Number: 4,758,563

[45] Date of Patent: Jul. 19, 1988

[54] 3-ALKOXY-2-AMINOPROPYAMINES, CARDIOVASCULAR COMPOSITIONS AND USE

[75] Inventors: Philip P. Grous, Philadelphia; Richard J. Mohrbacher, Maple Glen, both of Pa.

[73] Assignee: McNeilab, Inc., Springhouse, Pa.

[21] Appl. No.: 118,576

[22] Filed: Nov. 9, 1987

Related U.S. Application Data

[62] Division of Ser. No. 828,923, Feb. 12, 1986, Pat. No. 4,727,072.

[51] Int. Cl.$^4$ ............... C07D 295/12; A61K 31/445; A61K 31/535; A61K 31/40
[52] U.S. Cl. ............................ 514/233.8; 514/321; 514/331; 514/237.8; 544/148; 544/165; 546/197; 546/232; 548/526; 548/569
[58] Field of Search ............... 544/148, 165; 546/197, 546/232; 548/526, 569; 514/237, 321, 331

[56] References Cited

U.S. PATENT DOCUMENTS

| | | | |
|---|---|---|---|
| Re. 30,577 | 4/1981 | Busch et al. | 260/326.5 |
| 3,962,238 | 6/1976 | Mauvernay et al. | 548/564 |
| 4,430,338 | 2/1984 | Jansen et al. | 514/428 |
| 4,555,514 | 11/1985 | Combourieu et al. | 514/343 |
| 4,645,778 | 2/1987 | Monteil et al. | 548/569 |

Primary Examiner—Robert W. Ramsuer
Attorney, Agent, or Firm—David J. Levy

[57] ABSTRACT

Propylamines of the formula (I):

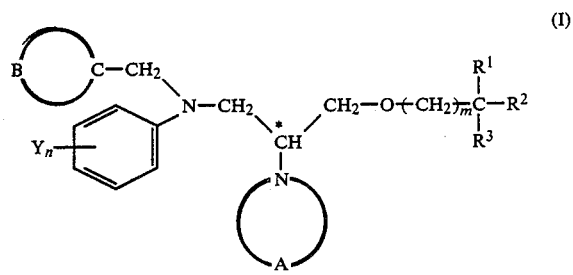

and isomers thereof, particularly those enantiomers and racemates relative to the chiral carbon indicated by an asterisk (*). The propylamines can be used for the treatment of hypertension or angina in humans. A is pyrrolidine, piperidine or morpholine and B is an aromatic heterocycle, aromatic carbocycle or saturated carbocycle.

17 Claims, No Drawings

3-ALKOXY-2-AMINOPROPYAMINES, CARDIOVASCULAR COMPOSITIONS AND USE

This application is a division of U.S. Ser. No. 828,923 filed Feb. 12, 1986, now U.S. Pat. No. 4,727,072.

Various ethers are known to be effective cardiovascular pharmaceuticals as described in U.S. Pat. No. 4,555,514; U.S. Pat. No. Re. 30,577; PCT Publication No. 83/02274; Australian Pat. No. 85/37537; French Brevet No. 2,558,159; and European Patent Application Nos. 138,684; 146,155 and 146,159.

SUMMARY OF THE INVENTION

Propylamines of the following formula (I):

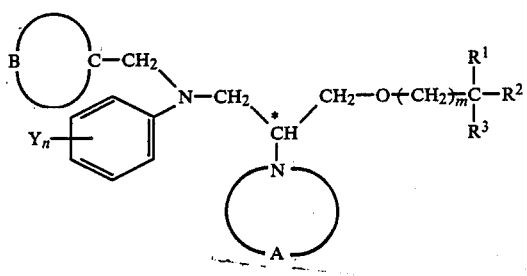

are provided as antihypertensive and anti-anginal agents which can be used in a manner similar to bepridil. In formula (I), $R^1$–$R^3$ are alkyl or joined to cycloalkyl, A is pyrrolidine, piperidine or morpholine, Y is as described, n is 0–3 and B is an aromatic or saturated ring with or without substitution.

DETAILED DESCRIPTION OF THE INVENTION

In more detail, the invention includes propylamines of the following formula (I):

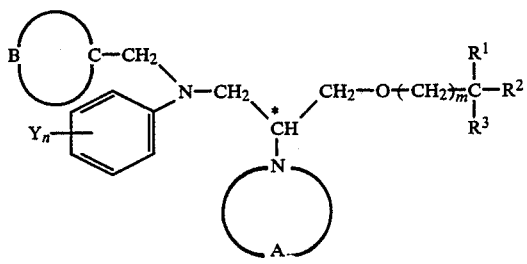

wherein
$R^1$, $R^2$ and $R^3$ are lower alkyl groups or $R^1$ is a lower alkyl group and $R^2$ and $R^3$ are joined to form a cycloalkyl group of about 3 to 7 carbons or $R^1$, $R^2$ and $R^3$ are joined to form a polycyclicalkyl group of about 7 to 12 carbons;
m is 0 or 1;
A represents the atoms necessary to form a pyrrolidine, piperidine or morpholine ring;
Y is independently selected from the group consisting of halo, alkyl, alkoxy, trifluoromethyl, hydroxy, or, when n is 2 on adjacent carbons, methylenedioxy;
n is 0, 1, 2 or 3; and
B represents the atoms necessary to form an aromatic heterocyclic ring, a saturated carbocyclic ring or an aromatic carbocyclic ring wherein said aromatic carbocyclic ring is either unsubstituted or is independently substituted by 1 or 2 of halo, alkyl, alkoxy, trifluoromethyl, hydroxy, monoalkylamino, dialkylamino or methylenedioxy;

and the pharmaceutically acceptable acid addition salts thereof.

Within the scope of $R^1$, $R^2$ and $R^3$ are lower alkyl groups of about 1 to 6 carbons such as methyl, ethyl, n-propyl and iso-propyl, the individual $R^1$, $R^2$ and $R^3$ groups being independently chosen, with methyl being particularly preferred. Thus, a particular alkoxymethyl group of the invention is that where $R^1$, $R^2$ and $R^3$ are all methyl. A second arrangement for $R^1$–$R^3$ is that where $R^1$ is an alkyl as described and $R^2$ and $R^3$ together represents a saturated hydrocarbon cyclic moiety of about 3 to 10 carbons, e.g. a cyclopentyl or cyclohexyl ring. A third arrangement for $R^1$–$R^3$ is where all three are part of a saturated hydrocarbon cyclic moiety, e.g. 1-adamantyl, 1-bicyclo[2.2.2]octane or 1-bicyclo[2.2.1]heptane.

m is, in particular, 1.

A represents particularly the atoms necessary to form a pyrrolidine ring.

Y is halo such as fluoro, chloro, bromo, or iodo; alkyl of about 1 to 6 carbons such as methyl, ethyl, n-propyl or tert-butyl; alkoxy of about 1 to 6 carbons such as methoxy, ethoxy or sec-butoxy; $CF_3$; OH; or when n is 2 at adjacent carbons, Y can be methylenedioxy.

n is 0–3, particularly 2 such as the 2 and 6 positions although all such positional isomers are contemplated, e.g. 2,3; 3,5; etc. Particular Y substitution includes 2,6-dichloro, 3-methoxy, 2-chloro, 2,6-dimethyl, 3-trifluoromethyl, 2,6-dibromo and 2-chloro-6-methyl.

B includes aromatic heterocyclic rings of 5 or 6 members, e.g. those having a single N, S or O as the heteroatom such as 2- or 3-pyrrolyl, 2- or 3-thienyl or 2- or 3-furanyl or 2-, 3- or 4-pyridinyl. Also within the scope of B are saturated carbocyclic rings of about 3 to 10 carbons such as cyclopropyl, cyclopentyl and cyclohexyl rings. The last group of B rings are the aromatic carbocyclic rings such as phenyl which may be unsubstituted or substituted independently by 1 or 2 of halo, such as fluoro, chloro, bromo or iodo; alkyl of about 1 to 6 carbons such as methyl or ethyl; alkoxy of about 1 to 6 carbons such as methoxy, ethoxy or tert-butoxy; $CF_3$; OH; monoalkylamino of about 1 to 6 carbons such as methylamino or sec-butylamino dialkylamino of about 2 to 12 carbons such as dimethylamino or N-sec-butyl-N-methylamino; or methylenedioxy at adjacent carbons. Particular examples of B ring groups are phenyl, 4-dimethylaminophenyl, 3,4-dimethoxyphenyl, 4-pyridinyl and cyclohexyl.

Particular examples of compounds of the invention of formula (I) are:

N-(2,6-dichlorophenyl)-beta-[[(1-methylcyclohexyl)methoxy]methyl]-N-(phenylmethyl)-1-pyrrolidineethanamine;

beta-[(2,2-dimethylpropoxy)methyl]-N-(3-methoxyphenyl)-N-(phenylmethyl)-1-pyrrolidineethanamine;

N-(2-chlorophenyl)-beta-[(2,2-dimethylpropoxy)methyl]-N-(phenylmethyl)-1-pyrrolidineethanamine;

N-(2,6-dichlorophenyl)-N-[[4-(dimethylamino)phenyl]methyl]-beta-[(2,2-dimethylpropoxy)methyl]-1-pyrrolidineethanamine;

N-(2,6-dichlorophenyl)-N-[(3,4-dimethoxyphenyl)methyl]-beta-[(2,2-dimethylpropoxy)methyl]-1-pyrrolidineethanamine;

N-(2,6-dichlorophenyl)-beta-[(2,2-dimethylpropoxy)methyl]-N-(phenylmethyl)-1-pyrrolidineethanamine;

N-(2,6-dichlorophenyl)-beta-[(2,2-dimethylpropoxy)-methyl]-N-(4-pyridinylmethyl)-1-pyrrolidineethanamine;

N-(2,6-dimethylphenyl)-beta-[(2,2-dimethylpropoxy)-methyl]-N-(phenylmethyl)-1-pyrrolidineethanamine;

beta-[(2,2-dimethylpropoxy)methyl]-N-(phenylmethyl)-N-[3-(trifluoromethyl)phenyl]-1-pyrrolidineethanamine;

beta-[(2,2-dimethylpropoxy)methyl]-N-phenyl-N-(phenylmethyl)-1-pyrrolidineethanamine;

N-(2,6-dichlorophenyl)-N-(phenylmethyl)-alpha-[[(tricyclo[3.3.1.1$^{(3,7)}$]dec-1-yl)methoxy]methyl]1-pyrrolidineethanamine;

N-(cyclohexylmethyl)-N-(2,6-dichlorophenyl)-beta-[(2,2-dimethylpropoxy)methyl]-1-pyrrolidineethanamine; or N-(2,6-dichlorophenyl)-beta-[(1,1-dimethylethoxy)methyl]-N-(phenylmethyl)-1-pyrrolidineethanamine.

Representative salts of the compounds of formula (I) which may be used include those made with acids such as hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin. Such salts can be made by reacting the free base of (I) with the acid and recovering the salt.

Compounds of Formula (I) and other compounds of the invention may exist in various isomeric forms, e.g., in view of the presence of an asymmetric carbon. Examples include the asymmetric carbon directly attached to the nitrogen of the pyrrolidine. It is understood that the present invention includes all such individual isomers and their racemates. Particular isomers are the R and S isomers relative to symmetry at the carbon in formulae (I), (V), (VI) and (VIa) below marked by an asterisk (*). Such individual isomers may be obtained as known in the art, e.g. by initiating the synthesis with optically active starting materials or reagents or by separation of racemic intermediates or final products, e.g. as described in "Stereochemistry of Carbon Compounds", by Ernest L. Eliel, McGraw-Hill, New York (1962).

Also within the scope of the invention are compounds of the invention in the form of hydrates and other solvate forms. "Alkyl" as used herein denotes straight and branched chain alkyl.

To prepare compounds of the present invention having formula (I), one may use the reaction sequences summarized in the following Reaction Scheme wherein R is used to refer to the —$(CH_2)_m$—$C(R^1R^2R^3)$ moiety in formula (I) and the remaining symbols are as defined for formula (I) compounds, e.g., the A and B rings, Y, etc.

Reaction Scheme:

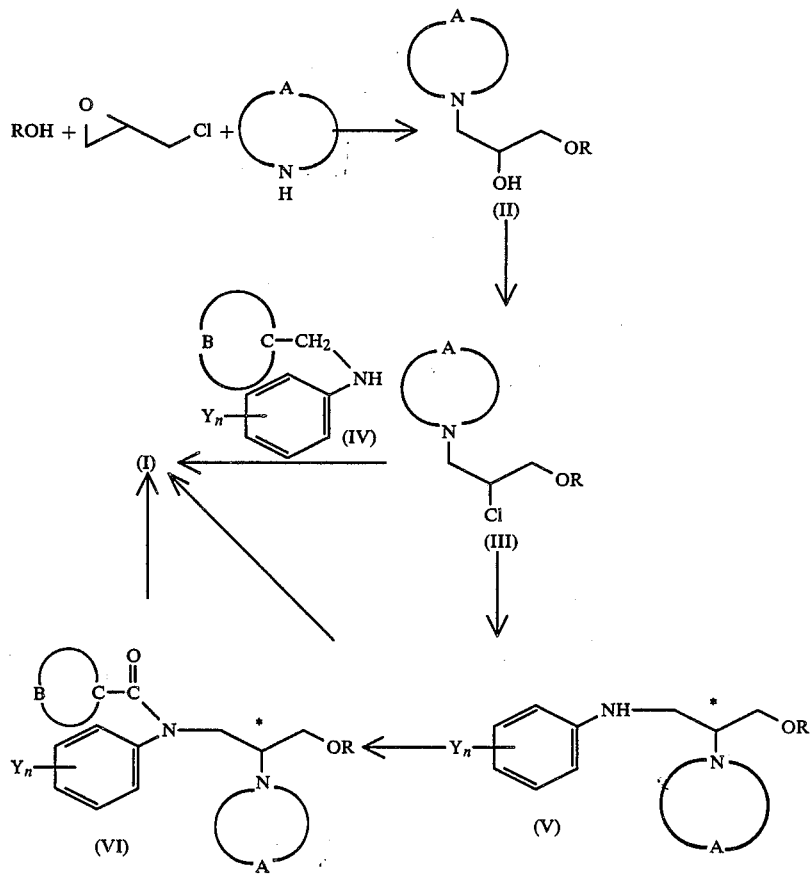

Alcohols of formula ROH may be obtained commercially, prepared as known in the art or synthesized from the corresponding acid of formula $(R^1R^2R^3C)COOH$ by reduction, e.g., with borane or other reducing agents. Epichlorohydrin and the A ring heterocyclic compound are commercially available or known in the literature.

Amino alcohols of the formula (II) may be prepared by stirring 1.0 mole of the starting alcohol ROH and 1.0 mole of epichlorohydrin and adding 0.001 mole of a Lewis Acid such as titanium (IV) chloride, zinc (II) chloride, boron trifluoride or tin (IV) chloride. The reaction temperature rises to about 160° C. in a few seconds and is stirred until the reaction temperature is about 40° C. followed by the addition of 1.0 mole of the A ring heterocycle. The reaction mixture is stirred and heated on a steam bath for 1 hr, allowed to return to room temperature and 25% sodium or potassium hydroxide solution containing 1 mole of hydroxide is added with stirring. The reaction mixture is heated on a steam bath for 30 min, then cooled to room temperature, partitioned between cold water and ether and the ether layer is dried, the solvent is removed and the residue distilled under reduced pressure to give the amino alcohol (II).

The intermediate (II) is then reacted with a chlorinating agent such as $PCl_5$, $PCl_3$ or $SOCl_2$ to yield the chloro compounds of formula (III). In a typical procedure, 109.4 g (0.525 m) of phosphorus pentachloride and 60 ml of dry toluene are stirred in an inert atmosphere and cooled in ice while a solution of 0.5 m of the amino alcohol (II) hydrochloride in 150 ml of dry toluene is added dropwise at a rate to keep the reaction temperature below 10° C. When the addition is complete, the ice bath is removed and stirring is continued at RT for 2 hrs. The resulting solution is added dropwise at a rate to keep the reaction temperature below 25° C. to a stirred solution of 4.5 m of potassium hydroxide in cold water while cooling in an ice bath. Stirring is continued for 30 min after the addition is complete and the reaction mixture is partitioned between toluene and water. Occasionally, an immiscible oily layer forms between the layers. In this case, the oil and the organic layers can be combined. The toluene layer or the toluene and oil layers are washed with water, dried and concentrated to dryness in vacuo at less than 50° C. The crude product is stored under argon in the refrigerator until used.

The chloro compound of formula (III) may then be directly reacted with a secondary aniline of formula (IV) to yield (I) or may be first reacted with a primary aniline of the formula $Y_n$-phenyl-$NH_2$ to yield (V). If a formula (V) compound is used, it may be directly reacted with a BC—$CH_2$—$LG^1$ compound to yield the product of formula (I), wherein $LG^1$ is a leaving group such as chloro or bromo. Alternatively, the compound of formula (V) may be reacted with a compound of formula BC—C(=O)—$LG^2$, wherein $LG^2$ is a leaving group such as a mixed anhydride or chloro, to yield an amide intermediate of formula (VI). The amide (VI) may be reduced by known reduction methods, e.g. borane reduction, to yield the product of formula (I). Reaction of the chloro compound (III) to yield (I) or (V) involves a transition state moiety formed by loss of Cl— and migration of the N-A ring to the carbon which formerly carried the chlorine.

In more detail, the reaction of (III) with the secondary aniline (IV) may be carried out by dropwise addition of a solution of 1.1 eq of (III) and 1.0 eq of secondary aniline (IV) in dry toluene at about 100° C. to a stirred mixture of 1 or more eq of sodium hydride and about 0.01 to 0.1 eq of potassium hydride in dry toluene under argon or nitrogen. The reaction mixture is stirred, heated to reflux for about 4 to 80 hrs, cooled to RT and partitioned between water and toluene and/or ether. The organic portion is purified by chromatography, distillation and/or crystallization. In an alternative procedure, a solution of 1.0 or more eq of methyl lithium in ether is added dropwise to a stirred solution of 1.0 eq of the secondary aniline (IV) in dry THF under argon or dry nitrogen. The reaction mixture is stirred for 1 or more hrs, a solution of 1.0 eq of (III) in dry tetrahydrofuran is added dropwise and the reaction mixture is heated to reflux for 3 to 16 hrs. The reaction mixture is cooled to RT, diluted with ether, extracted with water and the organic portion is purified by chromatography, distillation or crystallization.

Other alkyl lithium compounds that may be used in this alternative procedure are n-butyl lithium in hexane and sec-butyl lithium in cyclohexane.

In the second general method for synthesis of (I), intermediate (III) is reacted with the primary aniline $Y_n$-phenyl-$NH_2$ to produce (I). For example, to a stirred mixture of 1.1 eq of sodium hydride in dry toluene under argon or dry nitrogen is added a solution of 1.0 eq of the primary aniline in dry toluene. The reaction mixture is stirred and heated to reflux for 1 or more hrs, cooled, a solution of 1.0 eq of (III) in dry toluene added dropwise to the stirred reaction mixture and the reaction mixture stirred and heated to reflux for 4 or more hrs. It is then cooled to RT and extracted with water and dilute hydrochloric acid. The acid layers are combined, basified and extracted with ether and the organic portion is purified by chromatography, distillation and/or crystallization to give secondary anilines of type (V).

The intermediate (V) may then be reacted with the cyclic compound of the formula BC—$CH_2$—$LG^1$ to yield (I). In a general procedure, to a stirred solution of 1.0 eq of the secondary aniline (V) in dry THF under argon or dry nitrogen is added dropwise 1.1 or more eq of methyl lithium in ether at about −5° C. The cooling bath is removed, about 1.1 of BC—$CH_2$—$LG^1$, e.g. benzyl bromide, is added and the reaction mixture is stirred at RT for about 18 hrs. The reaction mixture is diluted with ether, extracted with water and dilute hydrochloric acid and the organic portion purified by chromatography, distillation and/or crystallization to give (I).

In the third approach to compound (I), an anion intermediate of a compound of the formula (V) is reacted with a compound of formula BC—C(=O)—$LG^2$ in a solvent such as THF by methods known to those skilled in the art of organic synthesis. The product of the reaction is the carbonyl compound of formula (VI). The carbonyl compound of formula (VI) may then be reduced by known reduction methods, e.g. borane reduction.

The activity of compounds of formula (I) for the treatment of hypertension was determined using the Spontaneously Hypertensive Rat (SHR) test as described below.

Spontaneously Hypertensive Rat Test

In this test, the arterial pressure of adult spontaneously hypertensive rats (Charles Rivers) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hr. A test compound is considered to be active as an antihypertensive agent if the mean arterial pressuer (MAP) indicates a fall of >15 mm of Hg. Each animals serves as its own control.

In addition to their utility in the treatment of hypertension, the compounds of formula (I) are useful in the treatment of the symptoms of angina pectoris by virtue of their ability to dilate coronary arteries. Their activity was measured using the "Lagendorff's isolated heart" preparation. This test has been described in "Pharmacological Experiments on Isolated Preparations", Staff of the Department of Pharmacology, University of Edinbourgh, 2nd Ed., Churchill Livingstone, N.Y., 1970, pp. 112–119. The test compounds were administered at concentrations of 30.0, 10.0, 3.0, 1.0, 0.3, 0.1, 0.03, and 0.01 micromolar ($10^{-6}$ molar).

The utility of compounds of the invention is demonstrated by results obtained in the above tests for compounds of formula (I) in the following Table I.

TABLE I

| Cpd of Example | Langendorff $EC_{30}(10^{-6}M)$ | SHR Dose | Route | δMAP |
|---|---|---|---|---|
| 1e | .0046 | 30 | po | −60 |
| 2d | .029 | 30 | po | −29 |
| 3b | .027 | 30 | po | −6 |
|  | .027 | 10 | ip | −52 |
| 4c | .0016 | 30 | po | −14 |
|  | .0016 | 10 | ip | −23 |
| 5 | .001 | 30 | po | −15 |
| 6 | .0073 | 30 | po | −33 |
| 7 | .028 | 30 | po | −37 |
| 8b | .0028 | 30 | po | −21 |
| 9b | .020 | 30 | PO | −28 |
| 10 | .005 | 30 | po | −13 |
|  | .005 | 10 | ip | −28 |
| 11c | .010 | 30 | po | −41 |
| 12 | .003 | 30 | po | −25 |
| 13 | .0043 | 30 | po | −20 |
|  | .0043 | 10 | ip | −74 |

The activity of compounds of formula (I) in the treatment of angina was also determined using the Myocardial Oxygen Supply and Demand (dog) Test as described below.

Myocardial Oxygen Supply and Demand Test

Mongrel dogs of either sex weighing between 8.4 and 12.3 kg were used for this study. These dogs were obtained from Haycock Farm, Quakertown, PA. They were anesthetized with pentabarbitol Na and ventilated with a Harvard positive pressure respirator (Model 607, Dover, MA) to maintain their blood pH and gaseous tension within physiological ranges. Heparin-filled polyethylene catheters were implanted into the right femoral artery (PE-260) and the right atrium (PE-180) for the measurement of their respective pressures. The right femoral vein was cannulated with a heparin-filled polyethylene catheter (PE-200) for drug infusion. A thoracotomy was then performed via the left fifth intercostal space. The left circumflex coronary artery was isolated from surrounding fascia and an electromagnetic flow transducer (I.D.=2.0 mm, Gould Statham Inc. Oxnard, CA) placed around it for the measurement of coronary blood flow. A Delmed intravenous catheter (18.5 ga.×8 in., Canton, MA) was inserted into the coronary sinus via a puncture wound made by an 18 ga. needle for coronary venous effluent blood sampling. Arterial oxygen samples were taken from the femoral arterial catheters. Total content of oxygen in whole blood was measured by the Lex-02-Con-TL (Lexington Instruments Corp., Waltham, MA). Myocardial oxygen consumption was estimated by the product of the difference in arterial and coronary sinus oxygen content and coronary blood flow through the left circumflex coronary artery. These techniques have been used extensively to study the effects of calcium channel blockers on myocardial oxygen supply and demand in various animal models. References for these techniques include Jolly, S. R. and Gross, G. J. Effect of FR 7534, A New Calcium Antagonist, On Myocardial Oxygen Demand. Euro. J. Pharm. 54: 289–293, (1979); Ono, H., Ohara, N, and Hashimoto, K. Effect of an Anti-Anginal Drug, Perhexiline, on Myocardial Oxygen Consumption in Anesthetized Open-Chest Dogs Compared With Verapamil and glyceryl Trinitrate. Jap. Cir. J. 46: 559–567 (1982); and Vater, W. and Schlossman, K. Effects of Nifedipine on the Hemodynamics and Oxygen Consumption of the Heart in Animal Experiments, in: Jatene and Lichtlen, 3rd International Adalat Symposium: New Therapy of Ischemic Heart Disease (Experta Medica, Amsterdam, Oxford), p. 33, (1975).

Arterial blood pH and gaseous tension were measured by a Corning pH/blood gas analyzer (Model 168, Medfield, MA). Arterial and atrial pressures were measured by connecting their respective catheters to Statham strain-gauge manometers (P23D, Gould Inc., Oxnard, CA). Gould-Statham electromagnetic blood flowmeters (Model SP2202, Oxnard, CA) were used to measure coronary blood flow. Lead II of the EKG was monitored continuously through subcutaneous insertion of stainless steel needle electrodes on the body surface of the animal. The EKG was recorded by a Grass oscillograph (Model 7D, Quincy, MA) with an EKG-pulse pre-amplifier (Model 7P6C) and a Polygraph D.C. driver amplifier (Model 7DAG). All the other recorded variables, i.e., arterial pressure, right atrial pressure and coronary blood flow were recorded by the Grass oscillograph. Coronary vascular resistance was calculated as the quotient of the difference in mean pressure (arterial—right atrial) and left circumflex blood flow. Heart rate was derived from the EKG averaged over a one-minute period.

Two doses for each compound tested were selected to induce vasodepressor responses in the animal of approximately 10 to 20% decrease in arterial pressure. The purpose was to normalize the differential effects of these compounds on afterload reduction such that any variations on oxygen demand induced by these agents could not be attributable to the difference in the reflex activation of the sympathetic adrenergic system. The two doses for each compound were infused sequentially and in a graded manner over a 10-minute period (5 min for each dose). Arterial and coronary sinus blood samples were taken at control, the end of infusion for each dose and at 15 min after the end of infusion. Arterial and atrial pressures, coronary blood flow and calculated vascular resistance as well as heart rate were monitored during these periods. Mean values and standard error of the means (SEM) were calculated and reported. The changes induced by the drugs were compared with the pre-drug control values and analyzed by the Student's t-test for paired comparison. Intergroup analyses were performed using the Student's t-test for unpaired comparison. The changes were considered significant at P levels of less than 0.05.

At 0.25 and 0.50 mg/kg, i.v., the product of Example 1e decreased arterial pressure by 8 and 15% and markedly increased myocardial oxygen supply/demand ratio by increasing coronary blood flow by 80 and 221% (p<0.05).

To prepare the pharmaceutical compositions of this invention, one or more compounds or salts thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 50 to about 1000 mg of the active ingredient, and, preferably, from about 100 to about 500 mg.

Also within the scope of the invention are novel intermediates, such as those of formula (VI) above, shown in more detail below as Formula (VIa):

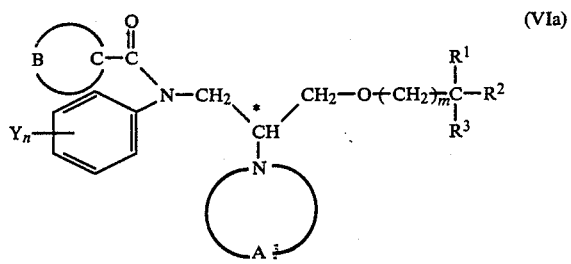

in particular where B represents a phenyl or substituted phenyl ring, and methods for the treatment of hypertension or angina pectoris by administration of pharmaceutically effective amounts of a compound of formula (I) in admixture with a pharmaceutically acceptable diluent or carrier.

In the following examples and throughout the specification, the following abbreviations may be used: mg (milligrams); g (grams); kg (kilograms); ml (milliliters); m (moles); mmole (millimoles); M (molar); N (normal); psi (pounds per square inch); mp (melting point); bp (boiling point); meq (milliequivalents); eq (equivalents); E (trans); Z (cis); $BH_3$ (borane); $B_2H_6$ (diborane); $Et_2O$ (diethyl ether); EtOAc (ethyl acetate); MeOH (methanol); EtOH (ethanol); LAH (lithium aluminum hydride); THF (tetrahydrofuran); DMF (dimethylformamide); MTBE (methyl tert-butyl ether); IPA (isopropyl alcohol); hr (hours); min (minutes); RT (room temperature); p.o. (per os, orally); i.p. (intraperitoneal); and C,H,N,O, etc. (the chemical symbols for the elements). Unless otherwise indicated, all temperatures are reported in °C. (degrees centigrade) and all references to ether are to diethyl ether.

EXAMPLE 1 a. 1-Methyl-1-cyclohexylmethanol

A three liter, three necked round bottom flask was equipped with a thermometer, magnetic stirrer, argon inlet and outlet adapters and a one liter addition funnel containing 922 ml of 1.0 molar $BH_3.THF$. 1-Methyl cyclohexanecarboxylic acid (119.2 g; 0.84 m) was added to the reaction vessel and dissolved in 100 ml of THF. The reaction mixture was cooled with an ice bath to 5° C. and the $BH_3.THF$ was added dropwise over 25 min maintaining the temperature between 5°–15° C. After the addition was complete, the ice bath was removed. After about five min, the reaction exothermed and foamed violently. A much slower addition rate and constant cooling should help to avoid this exotherm. The reaction was allowed to stir for two hr at RT under nitrogen, then 150 ml of methanol was added cautiously. When the foaming ceased, the reaction was concentrated in vacuo using low heat and the residue was treated with 100 ml of 5% acetic acid. After stirring for thirty min, the reaction was transferred to a one liter separatory funnel, diluted with water (slurry dissolved) and extracted three times with ether. The combined ether extracts were washed twice with saturated sodium bicarbonate, twice with brine, dried over anhydrous magnesium sulfate, filtered through celite and concentrated in vacuo (low heat) to give 79.09 g of a clear water-white oil. The oil was distilled on a Kugelrohr apparatus at 75°–130° C. (25 mm of Hg). Most distilled at 90° C. to give 72.11 g of 1-methyl-1-cyclohexylmethanol.

b. alpha-[((1-Methylcyclohexyl)methoxy)methyl]-1-pyrrolidineethanol

A two liter three necked round bottom flask was equipped with a mechanical stirrer, condenser, thermometer, two neck adapter, drying tube, and a nitrogen inlet. 1-Methyl-1-cyclohexylmethanol (71.2 g; 0.555 m) (the compound of Example 1a.) was added to the reaction vessel followed by 100 ml of xylene and 43.4 ml (0.555 m) of epichlorohydrin. The reaction was heated to 50° C. while stirring under nitrogen. 1.45 g (0.0056 m) of $SnCl_4$ was added. The reaction exothermed suddenly to 140° C. and slowly cooled to 50° C. The reaction was kept at 50° C. in a water bath for 1.5 hr, then cooled to 5° C. with an ice bath. Cold 20% sodium hydroxide (prepared from 40 g of 50% NaOH) was added followed by 47.4 g (0.666 m) of pyrrolidine. The ice bath was removed, the reaction was heated to reflux for one hr, cooled to RT, diluted with about one liter of water and extracted twice with ether. The combined ether extracts were washed with water, brine, dried over anhydrous potassium carbonate, filtered through dicalite and concentrated in vacuo to give 143.39 g of crude product a light yellow viscous oil. The crude oil was distilled twice to yield 77.6 g (55%) of the title compound, b.p. 139°–154° C. (0.025 mm).

c. 1-[2-Chloro-3-(1-methylcyclohexyl)methoxypropyl]-pyrrolidine

A 500 ml three necked round bottom flask was equipped with a mechanical stirrer, addition funnel, thermometer and an argon inlet and outlet. $PCl_5$ (33 g; 0.159 m) and 18 ml of dry toluene was added to the reaction vessel. 38.5 g (0.151 m) of alpha-[((1-methylcyclohexyl)methoxy)methyl]-1-pyrrolidineethanol (the compound of Example 1b.) was added to the addition funnel along with 45 ml of toluene. Hydrogen chloride gas was bubbled into the addition funnel until the solution was acidic. The $PCl_5$ suspension was cooled to 10° C. and the amino alcohol hydrochloride solution was added dropwise, maintaining the temperature between 10°–15° C. After the addition was complete, the ice bath was removed and the mixture stirred at RT for 1.5 hr. A two liter beaker containing 116 ml of 45% potassium hydroxide and 210 g of ice was cooled in an ice bath. The reaction mixture (a clear yellow solution) was transferred to a separatory funnel and added portionwise at a rate to keep the reaction temperature at 25°–35° C. Stirring was continued for 0.5 hr after the addition. The reaction was transferred to a two liter separatory funnel and diluted with water and ether. The water layer was extracted twice with ether and the combined ether extracts were washed twice with water, once with brine, dried over anhydrous potassium carbonate and concentrated in vacuo to give 29.12 g of the title compound.

d. N-Benzyl-2,6-dichloroaniline

A 100 ml three necked round bottom flask was equipped with a magnetic stirrer, water-cooled reflux condenser, heating mantle, and argon inlet and outlet adapters. Sodium hydride (3.25 g; 0.0677 m of 50%) was added to the reaction vessel, extracted twice with ether, and suspended in 62 ml of THF. 2,6Dichloroaniline (10.0 g; 0.0617 m) was added and the reaction was heated to reflux for two hr, cooled to RT, and benzyl bromide (10.6 g; 0.0617 m) was added dropwise over 15 min. The reaction was heated to reflux for one hr, cooled to RT and quenched with 2-propanol. The THF was removed in vacuo and the residue partitioned between ether and water. The ether layer was dried over anhydrous $K_2CO_3$ and evaporated in vacuo to give 15.5 g of the title compound.

e. N-(2,6-Dichlorophenyl)-beta[[(1-methylcyclohexyl)-methoxy]methyl]-N-(phenylmethyl)-1-pyrrolidineethanamine hydrochloride(1:1)

A 100 ml three necked flask was equipped with a magnetic stirrer, argon inlet and outlet, thermometer, addition funnel and a silicone oil bath. The apparatus was flame dried with argon purging through the system while assembled. Sodium hydride (2.39 g; 0.0498 m of a 50% oil dispersion) was added to the reaction vessel, extracted twice with anhydrous ether, suspended in 20 ml of diglyme and charged with about 20 mg of potassium hydride. The reaction was immersed in a silicone oil bath and heated to 110°–115° C. and kept there by a Thermowatch ®. N-Benzyl-2,6-dichloroaniline (10.45 g; 0.0415 m) (the product of Example 1d.) and 1-[2-chloro-3-(1-methylcyclohexyl)methoxypropyl]pyrrolidine (13.64 g; 0.0498 m) (the compound of Example 1c.) were combined in the addition funnel, diluted with 22 ml of diglyme and added dropwise over about 15 min. The reaction appeared as an orange-brown suspension. After the addition was complete, the reaction was allowed to run at 110°–115° C. for two hr. The reaction was cooled to RT and about 10 ml of water was added dropwise to destroy the excess hydride. When the foaming ceased, the diglyme was removed on a rotary evaporator. The dark brown residue was dissolved in ether and extracted three times with water, once with brine, dried over anhydrous potassium carbonate and concentrated in vacuo to give 29.01 g of crude product, a thick reddish-brown oil. The crude oil was loaded onto a Waters Prep 500LC, two silica columns. Solvent system: 92 hexane/8 acetone, 500 ml fractions. Flow rate: 0.25 liters/min. The product-containing fractions were combined and concentrated in vacuo to give 8.89 g of a thick yellow oil which was dissolved in 125 ml of ethyl acetate and acidified with HCl gas. The resulting crystals were filtered, washed with ether and air dried to give 8.11 g of a tan crystalline solid. The tan solid was recrystallized from methylene chloride/ethyl acetate to yield 6.59 g of the title compound, an off-white solid mp 172°–181° C.

Elemental Analysis, Calculated: C, 63.94; H, 7.47; N, 5.32. Found: C, 64.06; H, 7.50; N, 5.33.

EXAMPLE 2 a. N-Benzyl-m-anisidine

A one liter three necked round bottom flask was equipped with a mechanical stirrer, argon inlet and outlet, steam bath and an addition funnel. NaH (21.4 g of 50% oil dispersion, 0.447 m) was added under argon, extracted twice with anhydrous $Et_2O$ then suspended in 300 ml of THF. KH (100 mg) was added, heated the suspension to reflux and m-anisidine (50 g; 0.406 m) was added portionwise giving a smooth evolution of hydrogen. The reaction was refluxed for two hr (turns purple) then cooled to about 5° C. and 69.4 g (0.406 m) of benzyl bromide in 200 ml of THF was added dropwise over 30 min. The reaction was stirred at RT for two hr, quenched with 25 ml of water and concentrated in vacuo to give a red oil. This oil was dissolved in $Et_2O$, washed twice with water, once with brine, dried over anhydrous $K_2CO_3$ and concentrated in vacuo to give 86.73 g of a red oil. The red oil was distilled on a 1×20 cm Vigreaux column. The fraction distilling at 176°–185° C. (0.3 mm) yielded 41.24 g of nearly pure title compound.

b. α-[(2,2-Dimethylpropoxy)methyl]-1-pyrrolidineethanol

To a stirred mixture of 92.53 g (1.0 m) of epichlorohydrin and 88.15 g (1.0 m) of neopentyl alcohol was added 0.26 g (0.001 m) of stannic chloride. The reaction temperature rose to about 60° C. then exothermed to about 130° C. in a few seconds. The reaction mixture was stirred until the temperature receded to about 40° C. then 71.12 g (1.0 m) of pyrrolidine was added. The reaction mixture was stirred and heated to about 95° C. for 1 hr. After cooling the reaction mixture to RT, a mixture of 80 g of 50% sodium hydroxide solution and 80 g of ice was added. The reaction mixture was stirred and heated to 90° C. for 0.5 hr then cooled to RT. The reaction mixture was partitioned between 400 ml of ice water and 400 ml of ether. The organic layer was dried and concentrated in vacuo to give 181 g of oil. The oil was distilled (89°–115° C. at 0.25 mm) to give 136 g of oil that crystallized on standing, 99.1% pure by g.c.

c.
1-[2-Chloro-3-(2,2-dimethylpropoxy)propyl]pyrrolidine

Dry hydrogen chloride gas was bubbled into an ice-cooled solution of 107.7 g (0.5 m) of α-[(2,2-dimethylpropoxy)methyl]-1-pyrrolidineethanol (the product of Example 2b.) in 100 ml of dry toluene until 20.05 g (0.55 m) was taken up. This solution was added to a stirred ice-cooled suspension of 109.4 g (0.525 m) of phosphorous pentachloride in 60 ml of dry toluene (argon atmosphere) at a rate to keep the reaction temperature between 10°–15° C. After the addition was complete, the ice bath was removed and the reaction mixture was stirred for 1.5 hr. The reaction mixture was added to a stirred ice-cooled solution of 385 ml (4.5 m) of 45% potassium hydroxide and 700 ml of ice at a rate to keep the reaction temperature between 25°–35° C. The reaction mixture was stirred for 0.5 hr then extracted with toluene. An immiscible oil formed between the layers. The oil was partitioned between dichloromethane and water. The dichloromethane layer and the toluene layer above were combined, dried and concentrated to dryness to give 84.3 g of oil. The oil was distilled (65°–86° C. at 0.35 mm) to give 76.63 g of oily product.

d.
beta-[(2,2-Dimethylpropoxy)methyl]-N-(3-methoxyphenyl)-N-(phenylmethyl)-1-pyrrolidineethanamine (E)-2-Butenedioate (1:1)

A 200 ml three necked round bottom flask was equipped with a 125 ml addition funnel, thermometer, argon inlet and outlet, magnetic stirrer and a silicone oil bath. The apparatus was flame dried with argon purging while assembled. NaH (3.38 g of a 60% oil dispersion) was added and extracted twice with $Et_2O$, then suspended in 64 ml of diglyme and treated with about 30 mg of KH. The reaction was immersed in a 115° C. silicone oil bath and heated to about 105° C. N-benzyl-m-anisidine (13.7 g; 0.064 m) and 17.7 g (0.064 m) of the product of Example 2c were combined in the addition funnel with 20 ml of diglyme and added dropwise with stirring under argon over about 25 min. The reaction slowly exothermed to 120° C. Heating at 115° C. was continued for 1.75 hr. An additional portion of KH was added. Allowed to run another hr at 110° C. Added 1.69 g of 60% NaH (0.65 eq) allowed to run another 1 hr. There was then added 10 g (0.57 eq) of the product of Example 2c and allowed to run for another 2½ hr at 110° C. then cooled to RT and let stand overnight. There was then added another 1.69 g of NaH, a pinch of KH and 10 g of the product of Example 2c at 110° C., and the reaction was let run for 2 hr. The reaction was removed from the oil bath, cooled to RT and cautiously quenched with water (about 50 ml) and let stand at RT under argon. The run was concentrated on a rotary evaporator and the residue was partitioned between $Et_2O$ and water in a 500 ml separatory funnel. The aqueous layer was extracted twice with $Et_2O$ and the combined $Et_2O$ extracts were washed twice with water and once with brine, dried over anhydrous $K_2CO_3$, filtered through dicalite and concentrated in vacuo to give 40 g of crude free base, a red oil. The red oil was distilled on a Kugelrohr apparatus collecting the fraction boiling at 210° to 240° C. (1.1 mm) which was purified on a Water's Prep 500 using two silica columns; solvent system: 92 Hexane/8 acetone; Flow rate: 0.25 l/minute (about 300 ml fractions). Product eluted in fractions 10 to 16.

Fractions 10 to 16 were combined and concentrated in vacuo to give 8.78 g of a thick amber oil, the free base of the title compound.

8.00 of the free base was dissolved in MeOH. One equivalent of fumaric acid (2.26 g) was added and dissolved with heating. The MeOH was removed in vacuo and the residue was dissolved in boiling EtOAc and filtered through dicalite. The EtOAc was concentrated to about 50 ml and diluted to 150 ml with hexane. Seeded and let crystallize overnight at RT. The crystals were filtered, washed with hexane and air-dried with suction to give 10.39 g of crude fumarate salt, a beige crystalline solid. The crude salt was dissolved in EtOAc, filtered through dicalite, concentrated to about 30 ml and cooled to 5° C. in an ice bath. $Et_2O$ (anhydrous) was added to the cloud point and seeded. Let recrystallize standing in an ice bath for 4 hr. The crystals were filtered, washed with cold 50 $Et_2O$/50 EtOAc, air-dried with suction, then dried overnight in vacuo to give 7.72 g of a light beige crystalline solid, mp 81°–85° C.

Elemental Analysis, Calculated: C, 68.42; H, 8.04; N, 5.32. Found: C, 68.32; H, 8.08; N, 5.27.

EXAMPLE 3

N-Benzyl-2-chloroaniline

A one liter three necked round bottom flask was equipped with a mechanical stirrer, water cooled condenser, additional funnel, a steam bath, argon inlet and outlet. NaH 18.82 g (0.392 m of a 50% oil dispersion) was added and extracted twice with anhydrous $Et_2O$ then suspended in about 150 ml of THF. The mixture was heated to reflux with stirring, KH (20 mg) was added and then 2-chloroaniline (50 g; 0.392 m) in 75 ml of THF was added portionwise over 10 min allowing for the smooth evolution of hydrogen. After refluxing for 1.5 hr, the reaction was cooled to RT. Another three necked flask was equipped as above. Benzyl bromide (67.1 g; 0.392 m) was added to the reaction vessel and cooled to about 5° C. under argon. The reaction mixture from the first flask was transferred to the addition funnel via cannula under argon—it was necessary to dilute the solution with about 200 ml of THF because crystals began to form. The anion was added dropwise over 45 min to the benzyl bromide at 5° C., then stirred for 1.5 hr. The reaction was worked-up by diluting cautiously with 20 ml of water and transferring to a one liter separatory funnel with $Et_2O$ after removing the THF on a rotary evaporator. The water layer was extracted again with $Et_2O$ and the combined $Et_2O$ extracts were washed twice with brine, dried over anhydrous $K_2CO_3$ and concentrated in vacuo to give 94.35 g of a dark red-brown oil which partly crystallized on standing. The oil was distilled on a Kugelrohr apparatus (110° C.–135° C.; 0.05 mm Hg) to give 40.72 g of a yellow-orange oil which crystallized on standing, m.p. 35°–40° C.

b. N-(2-Chlorophenyl)-beta-[(2,2-dimethylpropoxy)methyl]-N-(phenylmethyl)-1-pyrrolidineethanamine Hydrochloride (1:1)

A 200 ml three necked round bottom flask was equipped with a 125 ml addition funnel, thermometer, argon inlet and outlet, magnetic stirrer and a silicone oil bath. The apparatus was flame-dried while assembled with argon purging throughout. NaH 3.38 g (0.07 m of a 50% oil dispersion) was added, extracted twice with anhydrous $Et_2O$, then suspended in 64 ml of diglyme. About 100 mg of KH was added and the suspension was heated to 110° C. via a silicone oil bath under argon. A solution of 14.6 g (0.064M) of N-benzyl-2-chloroaniline (the product of Example 3a) and 15.0 g (0.064 m) of the product of Example 2c in 20 ml of diglyme was added dropwise over about 20 min with stirring under argon. After 1.5 hr at 110° C., the reaction was cooled to RT, transferred to a one liter separatory funnel, diluted with water and extracted with $Et_2O$. The water layer was extracted again with $Et_2O$. The combined $Et_2O$ extracts were washed once with water, twice with brine, dried over anhydrous $K_2CO_3$ and concentrated in vacuo to give 28.24 g of crude free base, a reddish-brown oil. The crude free base was dissolved in 200 ml of EtOAc, acidified with HCl gas (pH about 6) and allowed to crystallize overnight at RT. The crystals were filtered, air-dried with suction to give 15.74 g of crude hydrochloride salt, a brown tacky solid. The crude hydrochloride salt was partially dissolved in 350 ml boiling EtOAc and filtered through dicalite to remove insoluble black tar, concentrated to about 150 ml and allowed to recrystallize at RT overnight. The crystals were filtered, washed with 50EtOAc/50$Et_2O$ then $Et_2O$ and air-dried with suction to give 11.41 g, a tan solid which was dissolved in 350 ml of boiling EtOAc, decolorized with Norit SB, filtered through dicalite and concentrated to about 100 ml. Let recrystallize at RT for 3 hrs. The crystals were filtered, air-dried with suction to give 9.32 g of an off-white crystalline solid which was dried in vacuo to give 9.27 g of title compound, mp=160°-161° C.

Elemental Analysis, Calculated: C, 66.51; H, 8.04; N, 6.21. Found: C, 66.58; H, 8.05; N, 6.20.

EXAMPLE 4 a. 4-(N,N-Dimethylamino)benzoyl chloride

The title compound was prepared as described by N. Harada et al. in J. Am. Chem. Soc. 97, page 5351 (1975).

b. N-(2,6-Dichlorophenyl)-beta-[(2,2-dimethylpropoxy)methyl]-1-pyrrolidineethanamine A one liter three necked round bottom flask was equipped with a mechanical stirrer, 125 ml addition funnel, steam bath, thermometer, argon inlet and outlet adapter. NaH (10.72 g; 0.268 m) (60% oil dispersion) was added to the reaction vessel under argon and extracted twice with $Et_2O$ (anhydrous). Diglyme (27 ml) was added and about 100 mg of KH and the slurry was heated to 60° C. while stirring under argon. 2,6-Dichloroaniline (41.32 g; 0.255 m) in 50 ml of diglyme was added dropwise over 20 min. After the addition was complete, the reaction was stirred at 60° C. for 40 min then heated to 90° C. and (70.0 g; 0.255 m) of the product of Example 2c was added dropwise over 15 min with vigorous stirring. The mixture was stirred for three hr then an additional 5.8 g (0.14 eq) of 2,6-dichloroaniline and NaH 1.5 g (0.14 eq) were added. The reaction was allowed to run for another 2 hr. The reaction was cooled to RT under argon and let stand overnight. 100 ml of water was slowly added to the reaction mixture then the diglyme was removed in vacuo. The residue was transferred to a one liter separatory funnel and partitioned between $CH_2Cl_2$ and water. The water layer was extracted two more times with $Ch_2Cl_2$ and the combined $CH_2Cl_2$ extracts were washed twice with brine, dried over anhydrous $K_2CO_3$, filtered through dicalite and concentrated in vacuo to give 107.87 g of a brown oil. The brown oil was distilled on a Kugelrohr apparatus at 129°-155° C. (0.1 mmHg) to give 96.56 g of distillate. 48.3 g of the distillate was loaded onto a Waters Prep. 500 LC with two silica columns. Elution conditions were: Flow Rate=270 ml/minute Soluent System=95 Hexane/5 Acetone; 500 ml Fractions. The product eluted in fractions 3→5. The remaining 48.3 g of distillate was chromatographed in the same way. The fractions were combined to give 75.35 g of title compound a clear, colorless oil.

c. N-(2,6-Dichlorophenyl)-N-[[4-(dimethylamino)phenyl]methyl]beta-[(2,2-dimethylpropoxy)methyl]-1-pyrrolidineethanamine Hydrochloride Hydrate (7:7:1)

A 500 ml 3-necked round bottom flask was equipped with a $H_2O$ cooled condenser, $N_2$ inlet, drying tube outlet, mechanical stirrer, steam bath and an addition funnel. NaH (1.23 g of a 60% oil dispersion, 0.031 m) was added to the reaction vessel under $N_2$ and extracted twice with anhydrous $Et_2O$. THF (28 ml) was added followed by a pinch of KH (25% oil dispersion). The suspension was heated to reflux under $N_2$ and the product of Example 4b. (10.0 g, 0.0278 m) in about 10 ml of THF was added dropwise over 15 min. After refluxing for one hr, the reaction was cooled to RT. The product of Example 4a (5.11 g, 0.0278 mole) was added as a solid portionwise over 5 min and the reaction was allowed to stir at RT overnight under $N_2$. The reaction was quenched with $H_2O$ and concentrated on a rotovap whereupon crystals formed. The solid residue was partitioned between $CH_2Cl_2$ and $H_2O$. The aqueous layer was extracted two more times with $CH_2Cl_2$ and the combined $CH_2Cl_2$ extracts were washed with brine two times, dried over anhydrous $K_2CO_3$, filtered through dicalite and concentrated in vacuo to give 13.51 g of a tan solid which was dissolved in about 75 ml of MeOH and recrystallized in an icebath. The crystals were filtered off, washed with cold MeOH, air dried with suction and dried in vacuo at RT overnight to give 5.90 g, of a beige crystalline solid, the amide form of the final product m.p.=143°-146° C.

5.86 g (0.0116 m) of the amide was dissolved in 25 ml of THF and heated to reflux and treated with 3.0 eq (35 ml) of 1M $BH_3$.THF dropwise over 15 min with stirring under $N_2$ and let run overnight. The reaction was quenched by the dropwise addition of 35 ml of MeOH and then concentrated on a rotovap. The residue was dissolved in 150 ml of MeOH and refluxed for 6 hr. The MeOH was removed in vacuo and the residue was partitioned between $CH_2Cl_2$ and $H_2O$. The $H_2O$ layer was extracted twice with $CH_2Cl_2$ and the combined $CH_2Cl_2$ extracts were washed twiçe with brine, dried over $K_2CO_3$, filtered through dicalite and concentrated in vacuo to give 5.44 g of the free base of the final product, an orange oil. The free base was dissolved in 20 ml of IPA, carefully acidified to pH 7 with ethereal HCl, and diluted to 100 ml with Et$_2$O and seeded. Allowed to crystallize overnight at −5° C. The crystals were filtered off, washed with ether and air-dried with suction to give 3.36 g which was recrystallized from IPA/Et$_2$O to give 2.29 g of the title compound, a white crystalline solid, mp 154°–155° C.

Elemental Analysis for HCl.1/7H$_2$O: Calculated: C, 61.01; H, 7.64; N, 7.90; H$_2$O, 0.48. Found: C, 61.13; H, 7.57; N, 7.63; H$_2$O, 0.45.

EXAMPLE 5

N-(2,6-Dichlorophenyl)-N-[(3,4-dimethoxyphenyl)methyl]-beta-[(2,2-dimethylpropoxy)methyl]-1-pyrrolidineethanamine-Hydrochloride (1:1)

A 500 ml three necked round bottom flask was equipped with a water cooled condenser, N$_2$ inlet, drying tube outlet, mechanical stirrer, steam bath and an addition funnel. NaH (60% oil dispersion) 1.23 g (0.031 m) was added to the reaction vessel under N$_2$ and extracted twice with anhydrous Et$_2$O. THF (28 ml) was added followed by about 20 mg of KH (25% oil dispersion). The suspension was heated to reflux under N$_2$. The product of Example 4b. (10.0 g, 0.0278 m) in 10 ml of THF was added dropwise over 20 min and the reaction was refluxed for 1 hr then cooled to RT. 3,4-Dimethoxybenzoylchloride (6.21 g; 0.031 m) in about 10 ml of THF was added dropwise to the slurry with stirring at RT under N$_2$ over about 10 min. The reaction was heated to reflux for 18 hrs. BH$_3$.THF (83 ml of 1M) was added dropwise to the refluxing reaction over 20 min. The reaction was refluxed for 4 hrs and cooled to RT and quenched by the dropwise addition of MeOH (25 ml). The solvents were removed in vacuo and the residue was dissolved in 200 ml of MeOH and refluxed for 4 hrs. The MeOH was removed in vacuo and the residue was partitioned between water and CH$_2$Cl$_2$. The water layer was extracted two more times with CH$_2$Cl$_2$ and the combined CH$_2$Cl$_2$ extracts were washed twice with brine, dried over anhydrous K$_2$CO$_3$, filtered through dicalite and concentrated in vacuo to give 14.08 g, of an amber oil which was partially dissolved in hot Et$_2$O, filtered through dicalite and acidified with ethereal HCl (total volume about 200 ml). The HCl salt oiled-out then solidified. The salt was filtered off, air-dried with suction to give 11.78 g of crude hydrochloride salt. The crude hydrochloride salt was dissolved in EtOAc, filtered through dicalite, concentrated to 25 ml, diluted to 100 ml with Et$_2$O, seeded and allowed to crystallize at RT overnight. The crystals were filtered off, washed with Et$_2$O and air-dried with suction to give a white crystalline solid, which was dried overnight at 2.5 mm Hg at RT to give 10.10 g of the title compound, m.p. 153°–153.5° C.

Elemental Analysis: Calculated as HCl: C, 59.40; H, 7.20; N, 5.13. Found: C, 59.29; H, 7.24; N, 5.07.

EXAMPLE 6

N-(2,6,Dichlorophenyl)-beta-[(2,2-dimethylpropoxy)methyl]-N-(phenylmethyl)-1-pyrrolidineethanamine Hydrochloride (1:1)

To a solution of 10 g (0.028 m) of N-(2,6-dichlorophenyl)-beta-[(2,2-dimethylpropoxy)methyl]-1-pyrrolidineethanamine (the compound of Example 4b) in 6 ml of dry THF cooled to −45° to −52° C. was added over 45 min to 24.3 ml (0.035 m) of 1.43M CH$_3$Li in diethyl ether. The solution was allowed to stir at −42° C. to −12° C. for 2.5 hrs then 6.67 g (0.039 m) of benzyl bromide was added over a few min. The reaction was stirred overnight, diluted with 200 ml of ether and then ice and water were added. The ether layer was washed first with water and then three 50 ml portions of 3N HCl. The middle layers (oil and crystals) of all three extractions were combined and cooled in an ice bath until crystallization was complete. After filtering, the product washed with a small amount of ether gave a cream-colored solid, 8.3 g. A 7.8 g sample of this solid was recrystallized from about 350 ml of H$_2$O after charcoal treatment to give 7.1 g, m.p. 170°–171° C. A final recrystallization from water gave 5.3 g of white plates, m.p. 171°–172° C.

Elemental Analysis C$_{25}$H$_{34}$N$_2$OCl$_2$.HCl: Calculated: C, 61.79; H, 7.26; N, 5.77. Found: C, 61,84; H, 7.31; N, 5.74.

EXAMPLE 7

N-(2,6-Dichlorophenyl)-beta-[(2,2-dimethylpropoxy)-methyl]-N-(4-pyridinylmethyl)-1-pyrrolidineethanamine Dihydrochloride A suspension of 6 g (0.017 m) of N-(2,6-dichlorophenyl)-beta[(2,2-dimethylpropoxy)methyl]-1-pyrrolidineethanamine (the compound of Example 4b.), 4.2 g (0.042 m) of triethylamine, 3.28 g (0.018 m) of 4-picolinoylchloride in 100 ml of dry toluene was stirred at gentle reflux for 2.5 hrs then for 18 hrs at 25° C. Ether (50 ml), then ice and water were added followed by 3N NaOH. The aqueous layer was separated and extracted twice with EtOAc. The combined organic solution was washed with water then brine, dried (Na$_2$SO$_4$ and charcoal) and evaporated to yield a dark oil 7.4 g. This sample was combined with 5.3 g from another run and dissolved in 25 ml of CH$_2$Cl$_2$ and this solution was applied to a silica flash column (2″×7¼″) containing 360 ml of silica gel and eluted with acetone:hexane 1:4. A 200 ml second fraction yielded 6 g of pure oily N-(2,6-dichlorophenyl)-N-[3-(2-methylpropoxy)-2-(pyrrolidinyl)propyl]-4-pyridinecarboxamide. A 4 g (0.0086 m) sample of the above 4-pyridinecarboxamide in 20 ml of THF was cooled in an ice bath and 26 ml of 1M (0.026 m) BH$_3$.THF in THF was added over 15 mins. The reaction was stirred for 3 hrs at 25° C. and one hr at reflux. Reaction was cooled to 10° C. and an additional 10 ml of 1M BH$_3$.THF was added. Reaction stirred at reflux for an additional 6 hrs and cooled. After addition of ice, 2 ml of methanol and 3 ml of 3N HCl was added and the solution stirred for 30 min. After making basic with 50% then 3N NaOH, the solution was extracted three times with CH$_2$Cl$_2$; extracted aqueous three times with EtOAc and combined all organic extracts (dried Na$_2$SO$_4$) and evaporated solvents off the give 3.35 of oil. Added ether to warm isopropanolic-ethereal HCl solution of the 3.35 g of oil. After cooling 3.1 g of crystalline HCl salt was collected. Recrystallizations from acetonitrile-ether then acetonitrile gave white plates (1.3 g) of title compound m.p. 227° C. (softens), melt 230°–23° C. (dec.)

Elemental Analysis C$_{24}$H$_{33}$N$_3$Cl$_2$O.2HCl: Calculated: C, 55.08; H, 6.74; N, 8.03. Found: C, 55.31; H, 6.85; N, 8.09.

EXAMPLE 8 a.
N-(2,6-Dimethylphenyl)-beta-[(2,2-dimethylpropoxy)-methyl]-1-pyrrolidineethanamine A mixture of 3.96 g (0.165 m) of sodium hydride and 18.18 g (0.15 m) of 2,6-dimethylaniline in 200 ml of dry toluene was stirred and heated to reflux (argon atmosphere) for 1 hr. While the reaction mixture was still hot, a solution of 35.07 g (0.15 m) of 1-[2-chloro-3-(2,2-dimethylpropoxy)propyl]pyrrolidine, the product of Example 2c., in 25 ml of toluene was added dropwise over a period of 0.5 hr. The reaction mixture was stirred and heated to reflux for 20 hr, cooled to RT, diluted with 200 ml of ether and extracted with seven portions of water and five portions of 3N hydrochloric acid. The acid layers were combined, cooled, made basic with 50% sodium hydroxide solution and extracted with ether. The ether extract was dried and concentrated in vacuo to give 38.18 g of oil. The oil was distilled (149°–155° C. at 0.15 mm) to give 18.00 g of oil which was further purified by chromatography on a Waters Prep 500 LC with acetone/hexane (1:8) to give 15.33 g of oil. (GC=24% of alpha-isomer, 75% of beta-isomer).

b.
N-(2,6-Dimethylphenyl)-beta-[(2,2-dimethylpropoxy)-methyl]-N-(phenylmethyl)-1-pyrrolidineethanamine Hydrochloride To a stirred solution of 14.31 g (0.045 m) of N-(2,6-dimethylphenyl)-beta-[(2,2-dimethylpropoxy)methyl]-1-pyrrolidineethanamine (the product of Example 8a.) in 100 ml of dry tetrahydrofuran (argon atmosphere) was added dropwise 40 ml of 1.5M methyl lithium (0.06 m) in ether. The reaction mixture was stirred for 0.5 hr. The reaction mixture was cooled and 7.69 g (0.045 m) of benzyl bromide was added dropwise at about 20° C. The reaction mixture was stirred at RT for 1.5 hr. The reaction mixture was diluted with 100 ml of ether and extracted with water. The organic layer was extracted with four portions of 3N hydrochloric acid. A solid formed between the layers which was removed by filtration to give 5.30 g of tan solid. The solid was dissolved in toluene/chloroform, the chloroform was boiled off and the solution was cooled to crystallize the product. The solid was recrystallized from tetrahydrofuran to give 3.78 g of solid. This solid was combined with 1.23 g of identical solid similarly prepared and recrystallized from tetrahydrofuran/ether to give 4.52 g of light tan solid, m.p. 198°–199° C.

Elemental Analysis for $C_{27}H_{41}ClN_2O$: Calculated: C, 72.86; H, 9.28; Cl, 7.97; N, 6.29. Found: C, 72.94; H, 9.33; Cl, 8,03; N, 6.28, 6.26.

EXAMPLE 9 a.
beta-[(2,2-Dimethylpropoxy)methyl]-N-[3-trifluoromethyl)phenyl]-1-pyrrolidineethanamine Into a 500 ml three neck flask (argon atmosphere) was placed 3.17 g of 50% sodium hydride/mineral oil (0.06 m). The solid was washed with ether to remove the mineral oil, suspended in 100 ml of dry toluene and the suspension was stirred while 9.76 g (0.06 m) of 3-(trifluoromethyl)aniline was added. The reaction mixture was stirred and heated to reflux for 1 hr. The heat was reduced to about 90° C. and a solution of 14.03 g (0.06 m) of 1-[2-chloro-3-(2,2-dimethylpropoxy)propyl]pyrrolidine, the product of Example 2c., in 20 ml of dry toluene was added to the stirred reaction mixture. The reaction mixture was heated to reflux for 4 hr, cooled to RT, diluted with 200 ml of ether and extracted with four portions of water and six portions of 3N hydrochloric acid. The organic layer was washed with 3N sodium hydroxide solution, dried and concentrated in vacuo to give 19.12 g of oil. The oil was purified by flash chromatography with acetone/hexane (1:9) to give 13.16 g of oil GC=89.5%.

b.
beta-[(2,2-Dimethylpropoxy)methyl]-N-(phenylmethyl)-N-[3-(trifluoromethyl)phenyl]-1-pyrrolidineethanamine Hydrochloride A solution of 12.90 g (0.036 m) of beta-[(2,2-dimethylpropoxy)methyl]-N-[3-(trifluoromethyl)phenyl]-1-pyrrolidineethanamine (the compound of Example 9a.) in 100 ml of dry THF was stirred and cooled in an ice/ethanol bath (argon atmosphere) while 32 ml of 1.25M methyl lithium in ether (0.04 m) was added dropwise. The cooling bath was removed and stirring was continued for 0.5 hr. To the stirred reaction mixture was added 6.50 g (0.038 m) of benzyl bromide. The reaction mixture was stirred at RT for 18 hr, diluted with 100 ml of ether and extracted with three portions of water. The organic layer was extracted with four portions of 3N hydrochloric acid, dried and concentrated in vacuo to give 18.56 g of oil. The oil was dissolved in ether, extracted with 3N sodium hydroxide solution, dried and concentrated in vacuo to give 14.74 g of oil. The oil was purified by flash chromatography on silica gel with acetone/hexane (1:14) to give 5.76 g of oil. The oil was converted to the hydrochloride salt in toluene/ether and crystallized by the addition of hexane to give 5.79 g of white solid, m.p.=163.5°–165° C., the title compound.

Elemental Analysis for $C_{26}H_{36}ClF_3N_2O$: Calculated: C, 64.38; H, 7.48; Cl, 7.31; N, 5.78. Found: C, 64.45; H, 7.52; Cl, 7.35; N, 5.78.

EXAMPLE 10

β-[(2,2-Dimethylpropoxy)methyl]-N-phenyl-N-(phenylmethyl)-1-pyrrolidineethanamine (E)-2-Butenedioate (1:1)

A mixture of 9.16 g (0.05 m) of benzyl aniline, 1.44 g. (0.06 m) of sodium hydride and a small scoop of potassium hydride/mineral oil in 100 ml of dry toluene (argon atmosphere) was stirred and heated to 95° C. while 12.86 g (0.055 m) of the product of Example 2c. was added dropwise. The reaction mixture was stirred and heated to 100° C. for 60 hr. The reaction mixture was cooled to RT and partitioned between ether and water. The organic layer was dried and concentrated to dryness to give 20.80 g of oil, a mixture. A solution of 11.98 g of the reaction product mixture in 50 ml of dry toluene was treated with 2.55 g (0.0255 m) of succinic anhydride. The reaction mixture was heated to reflux for 7 hr, diluted with 75 ml of ether and extracted with three 75 ml portions of 25% potassium hydroxide. The organic soluble portion was dried and concentrated in vacuo to give 13.20 g of oil. The oil was purified by Kugelrohr distillation (160°–190° C. at 0.15 mm) to give 12.64 g of oil. The oil was purified by flash chromatography on silica using 2–5% acetone/hexane as the eluant to give 6.43 g of oil. (GC=0.08% α-isomer and 98.9% β-isomer). The oil was converted to the fumarate salt in isopropanol and crystallized by the addition of hexane to give 7.16 g of white solid. m.p.=116°–119.5° C., the title compound.

Elemental Analysis for $C_{29}H_{40}N_2O_5$: Calculated: C, 70.13; H, 8.12; N, 5.64. Found: C, 70.20; H, 8.16; N, 5.64.

EXAMPLE 11 a.

alpha-[[(Tricyclo[3.3.1.1.$^{3,7}$]dec-1-yl)methoxy]methyl]-1-pyrrolidineethanol To a stirred solution of 33.25 g (0.2 m) of 1-adamantane methanol and 18.15 g (0.2 m) of epichlorohydrin in 30 ml of xylene (warmed to 55° C.) was added 0.65 g (0.0025 m) of tin(IV) chloride all at once. The reaction exothermed to about 140° C. and stirring was continued for 1 hr. The reaction mixture was cooled to 5° C. and a solution of 15.29 g of 50% sodium hydroxide solution in 30 g of ice was added. Pyrrolidine (14.22 g, 0.2 m) was added and the reaction mixture was stirred and heated on a steam bath for 1.5 hr then cooled to RT and diluted with 150 ml of ether. The resulting solution was extracted with water and 3N hydrochloric acid. The acid layers were combined, basified and extracted with chloroform. The organic extract was dried and concentrated in vacuo to give 51.83 g of the title compound, an oil.

b.

1-(2-Chloro-3-[[(tricyclo[3.3.1.1.$^{3,7}$]dec-1-yl)methyl]-propyl)pyrrolidine

A solution of 51.83 g (0.175 m) of the crude amino alcohol from Example 11a in 100 ml of toluene was treated with gaseous HCl until 6.4 g (0.175 m) was taken up. This solution was added dropwise over a 20 min period to a stirred mixture of 37.48 g (0.18 m) of phosphorous pentachloride in 100 ml of toluene at 5°–15° C. The cooling bath was removed and stirring was continued for 1.5 hr. The resulting solution was added dropwise with stirring and cooling to 134.6 ml of 45% potassium hydroxide solution and 270 g of ice at a rate to keep the reaction temperature between 10°–15° C. The reaction mixture was diluted with 100 ml of ether and 100 ml of toluene, stirred for 0.5 hr and the layers were separated. The aqueous layer was washed with ether/toluene (1:1). The organic layers were combined, washed with saturated potassium carbonate, dried and concentrated in vacuo to give 48.04 g of the title compound, an oil.

c.

N-(2,6-Dichlorophenyl)-N-(phenylmethyl)-alpha-[[(tricyclo-[3.3.1.1.$^{3,7}$]dec-1-yl)methoxy]methyl]-1-pyrrolidineethanamine Hydrochloride (1:1)

A mixture of 1.26 g (0.042 m) of 80% sodium hydride/oil and a small scoop of 35% potassium hydride/oil in 80 ml of dry diglyme was stirred and heated to 115°–120° C. while a solution of 10.09 g (0.04 m) of N-benzyl-2,7-dichloroaniline (the compound of Example 1d) and 12.48 g (0.04 m) of the chloramine from Example 11b in 80 ml of dry diglyme was added dropwise over a 40 min period. Stirring was continued for 1.5 hr at 125° C. Methanol (5 ml) was cautiously added and the reaction mixture was concentrated in vacuo to give a dark oil. The oil was partitioned between ether and water. The organic part was extracted with 3N hydrochloric acid (an immiscible oil formed between the acid and organic layers). The oil and aqueous parts were combined and extracted with chloroform. The chloroform part was washed with 3N sodium hydroxide and saturated potassium carbonate, dried and concentrated in vacuo to give 12.38 g of dark oil. The oil was purified on a Waters Prep 500 LC with acetone/hexane (1:14) to give 5.30 g of oil. The oil was converted to the hydrochloride salt and crystallized from methyl-t-butyl ether/ether to give 3.75 g of solid title compound, m.p.=164.5°–166° C.

Elemental Analysis $C_{31}H_{40}Cl_2N_2O.HCl$: Calculated: C, 66.01; H, 7.33; Cl, 18.86; N, 4.97. Found: C, 65.95; H, 7.34; Cl, 18.87; N, 4.95.

EXAMPLE 12

N-(Cyclohexylmethyl)-N-(2,6-dichlorophenyl)-beta-[(2,2-dimethylpropoxy)methyl]-1-pyrrolidineethanamine (E)-2-Butenedioate Hydrate (20:25:2)

A 500 ml 3-necked round bottom flask was equipped with a $H_2O$ cooled condenser, $N_2$ inlet, drying tube outlet, mechanical stirrer, steam bath and an addition funnel. NaH (60% oil dispersion) (1.23 g, 0.031 m) was added to the vessel under $N_2$ and extracted twice with anhydrous $Et_2O$. THF (28 ml) was added followed by about 20 mg of KH. The suspension was heated to reflux under $N_2$. The product of Example 4b. (10.0 g, 0.0278 m) in 10 ml of THF was added dropwise over 20 min. The reaction that was initially greenish-yellow appears as a brown slurry after 1 hr of reflux. Cooled to RT. Cyclohexanecarboxylic acid chloride (4.55 g, 0.031 m) in 10 ml of THF was added dropwise over 15 min then the reaction was heated to reflux while stirring under $N_2$ overnight. The THF was removed in vacuo and 83 ml of 1 molar $BH_3.THF$ was added dropwise with stirring under $N_2$ while heating (steam bath). The reaction was refluxed for 4 hr. The THF was removed in vacuo, the residue was heated on a steam bath and 300 ml of MeOH was added dropwise with caution. The reaction was refluxed for 4 hr, concentrated in vacuo, partitioned between $H_2O$ and $CH_2Cl_2$. The $CH_2Cl_2$ layer was washed three times with brine, dried over anhydrous $K_2CO_3$ and concentrated in vacuo to give 11.94 g of the free base of the title compound, a clear orange oil. The fumarate was obtained by dissolving the oil in MeOH and treating it with 1.0 eq. of fumaric acid (2.92 g). The mixture was heated on a steam bath until a solution was obtained. The MeOH was removed in vacuo and the residue was triturated with hexane 5 times to obtain a tacky glass which was dissolved in 20 ml of THF and diluted to 125 ml with $Et_2O$, let crystallize for 3 hr at RT then put in refrigerator overnight. The crystals were filtered off and air-dried with suction to give 6.10 g, of an off-white crystalline solid which was dried at 60° C. (2 mm Hg) for 2 hr to give 6.06 g of the title compound m.p. 110°–112° C.

Elemental Analysis for 1¼ fumarate.1/10 $H_2O$: Calculated: C, 59.82; H, 7.56; N, 4.65; $H_2O$ 0.30. Found: C, 59.89; H, 7.66; N, 4.44; $H_2O$ 0.32.

EXAMPLE 13 a.

1-[3-(1,1-Dimethylethoxy)-2-hydroxypropyl]pyrrolidine

A mixture of 100.0 g (1.35 m) of tert. butyl alcohol and 51.4 g (1.35 m) of epichlorohydrin in 240 ml of xylenes was stirred and heated to 50° C. Tin (IV) chloride (3.5 g; 1.6 ml; 0.031 m) was added all at once and the reaction mixture immediately exothermed to about 100° C. The reaction mixture was stirred at about 50° C. for 1.5 hrs then cooled to 5° C. while a mixture of 97 g of 50% sodium hydroxide solution and 195 g of ice was added followed by 115.1 g (1.62 m) of pyrrolidine. The reaction mixture was stirred and heated to reflux for 1 hr. The reaction mixture was cooled to RT, diluted with 1 liter of water and extracted with ether. The ether soluble portion was dried and concentrated in vacuo to give 92.4 g of oil which was distilled at 97.5°–97° C./0.075 mm to yield 63.85 g of the title compound.

b.
1-[2-Chloro-3-(1,1-dimethylethoxy)propyl]pyrrolidine

To a stirred, cooled suspension of 34.7 g (0.167 ml) of phosphorous pentachloride in 20 ml of dry toluene (argon atmosphere) was added a solution of 31.93 g (0.159 m) of 1-[3-(1,1-dimethylethoxy)-2-hydroxypropyl]pyrrolidine (the product of Example 13a) and excess hydrogen chloride (gas) in 46 ml of dry toluene and 50 ml of dry tetrahydrofuran at a rate to keep the reaction temperature at 10°–25° C. When the addition was completed, the cooling bath was removed and the reaction mixture was stirred at ambient temperature for 1.5 hr. The reaction mixture was added portionwise, with stirring to a cooled solution of 122 ml of 45% potassium hydroxide and 230 g of ice at a rate to keep the reaction temperature at 25°–35° C. The reaction mixture was partitioned between ether and water. The ether portion was dried and concentrated in vacuo to give 31.69 g of oily title compound.

c.
N-(2,6-Dichlorophenyl)-beta[(1,1-dimethylethoxy)methyl]-N-(phenylmethyl)-1-pyrrolidineethanamine Hydrochloride (1:1)

In a 200 ml three neck, round bottom flask (argon atmosphere) was placed 50 ml of dry diglyme and 3.41 g (0.07 m) of 50% sodium hydride/mineral oil (washed free of oil with dry ether). The reaction mixture was stirred and heated to 110° C. while a solution of 15.7 g (0.071 m) of 1-[2-chloro-3-(1,1-dimethylethoxy)propyl]-pyrrolidine (the product of Example 13b) and 14.98 g (0.059 m) of N-benzyl-2,6-dichloroaniline in 20 ml of dry diglyme was added dropwise over a 30 min period. The reaction mixture was heated at 100° C. for another 30 min then cooled to RT. The excess sodium hydride was decomposed by the careful addition of 5 ml of water then the solvent was removed under vacuum on a rotary evaporator. The residue was partitioned between ether and water. The ether soluble part (25.0 g of oil) was purified by chromatography on a Waters Prep-500 liquid chromatograph using two silica gel columns, solvent system=hexane/ethyl acetate (4:1) to give 15.18 g of oily free base. The free base was converted to hydrochloride salt in ethyl acetate and recrystallized from dichloromethane/ethyl acetate to give 10.15 g of white solid, mp 175°–176° C.

Elemental Analysis for $C_{24}H_{32}ClN_2O/HCl$: Calculated: C, 61.09; H, 7.05; N, 5.94: Found: C, 61.05; H, 7.05; N, 5.89.

What is claimed is:
1. A propylamine of the following formula (I):

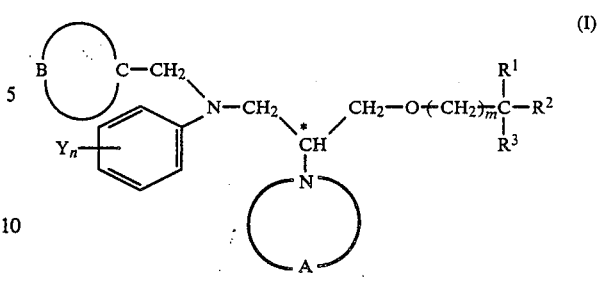

(I)

wherein
$R^1$, $R^2$ and $R^3$ are lower alkyl groups;
m is 0 or 1;
A represents the atoms necessary to form a pyrrolidine, piperidine or morpholine ring;
Y is independently selected from the group consisting of halo, alkyl, alkoxy, trifluoromethyl, hydroxy, or, when n is 2 on adjacent carbons, methylenedioxy;
n is 0, 1, 2 or 3; and
B represents the atoms necessary to a saturated carbocyclic ring;
and the pharmaceutically acceptable acid addition salts thereof.
2. The propylamine of claim 1, wherein
$R^1$, $R^2$ and $R^3$ are lower alkyl groups of about 1 to 6 carbons each;
m is 0 or 1;
A represents the atoms necessary to form a pyrrolidine ring;
Y is fluoro, chloro, bromo, iodo, alkyl of about 1 to 6 carbons, alkoxy of about 1 to 6 carbons, trifluoromethyl, hydroxy or methylenedioxy;
n is 0, 1, 2 or 3; and
B represents the atoms necessary to form a 5- or 6-membered saturated carbocyclic ring.
3. The propylamine of claim 2, wherein
$R^1$, $R^2$ and $R^3$ are each methyl;
m is 1;
Y is chloro, methyl, methoxy or trifluoromethyl; and
B represents the atoms necessary to form a cyclohexyl ring.
4. The propylamine of claim 1, wherein n is 2, Y is chloro, methyl, methoxy or trifluoromethyl.
5. The propylamine of claim 4, wherein Y is chloro at the 2 and 6 positions.
6. The propylamine of claim 1, wherein $R^1$ and $R^3$ are each methyl.
7. The propylamine of claim 1, wherein $R^1$ is lower alkyl.
8. The propylamine of claim 1, wherein said propylamine is the R isomer with respect to the carbon marked by the asterisk (*).
9. The propylamine of claim 1, wherein said propylamine is the S isomer with respect to the carbon marked by the asterisk (*).
10. The propylamine of claim 1, wherein said pharmaceutically acceptable acid addition salt is one formed with acids such as hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin.

11. The propylamine of claim 1, wherein said propylamine is N-(cyclohexylmethyl)-N-(2,6-dichlorophenyl)-beta-[(2,2-dimethylpropoxy)methyl]-1-pyrrolidineethanamine; or a pharmaceutically acceptable acid addition salt thereof.

12. The propylamine of claim 10, wherein said salt is the hydrochloride salt.

13. A pharmaceutical composition which comprises a propylamine of claim 1 in association with a pharmaceutically acceptable diluent or carrier.

14. A method for the treatment of hypertension in a mammal which comprises administering to the mammal the composition of claim 13.

15. The method of claim 14, wherein said mammal is a human.

16. A method for the treatment of angina in a mammal which comprises administering to the mammal the composition of claim 13.

17. The method of claim 16, wherein said mammal is a human.

* * * * *

UNITED STATES PATENT AND TRADEMARK OFFICE
CERTIFICATE OF CORRECTION

PATENT NO. : 4,758,563

DATED : July 19, 1988

INVENTOR(S) : Philip P. Grous et al.

It is certified that error appears in the above-identified patent and that said Letters Patent is hereby corrected as shown below:

Claim 1, column 24, lines 23-24, "B represents the atoms necessary to a saturated carbocyclic ring;" should read -- B represents the atoms necessary to form a saturated carbocyclic ring; --

Signed and Sealed this

Twenty-third Day of April, 1991

Attest:

HARRY F. MANBECK, JR.

*Attesting Officer*  *Commissioner of Patents and Trademarks*